(12) United States Patent
De Haan

(10) Patent No.: US 6,368,891 B1
(45) Date of Patent: Apr. 9, 2002

(54) METHOD FOR MANUFACTURING AN ELEMENT FORMED WITH SEMICONDUCTOR(S) AND FIRE DETECTOR COMPRISING SUCH AN ELEMENT

(76) Inventor: André De Haan, Avenue du 23 Août, 8 - B - 7000 Mons (BE)

( * ) Notice: Subject to any disclaimer, the term of this patent is extended or adjusted under 35 U.S.C. 154(b) by 0 days.

(21) Appl. No.: 09/242,541
(22) PCT Filed: Aug. 19, 1997
(86) PCT No.: PCT/BE97/00093
  § 371 Date: Apr. 26, 1999
  § 102(e) Date: Apr. 26, 1999
(87) PCT Pub. No.: WO98/08084
  PCT Pub. Date: Feb. 26, 1998

(30) Foreign Application Priority Data

Aug. 19, 1996 (BE) .............................................. 9600704

(51) Int. Cl.⁷ .......................... H01L 21/66; G01R 31/26
(52) U.S. Cl. ........................................... 438/57; 438/48
(58) Field of Search ............................... 438/56, 57, 48

(56) References Cited

U.S. PATENT DOCUMENTS

| | | | | |
|---|---|---|---|---|
| 4,381,922 A | * | 5/1983 | Frey et al. ..................... 422/98 |
| 5,039,561 A | * | 8/1991 | Debe ........................ 427/255.6 |
| 5,336,558 A | * | 8/1994 | Debe .......................... 428/323 |

* cited by examiner

*Primary Examiner*—Vu A. Le
*Assistant Examiner*—Bradley K. Smith
(74) *Attorney, Agent, or Firm*—Schnader Harrison Segal & Lewis LLP

(57) ABSTRACT

The invention concerns a method for manufacturing an element formed with semi-conductor(s) for fire detection which consists in applying by evaporation under vacuum on an insulating substrate a phtalocyanine film, which is solidified so as to obtain on the surface of the semiconductor acceptors and donors in such proportion as to enable the detection of a fire with or without flames.

12 Claims, 9 Drawing Sheets

α-CuPc

β-CuPc

METHOD FOR MANUFACTURING AN ELEMENT FORMED WITH SEMICONDUCTOR(S) AND FIRE DETECTOR COMPRISING SUCH AN ELEMENT

The invention relates to a method for forming a semiconductor element enabling the detection of a fire with or without flame, according to which a phthalocyanine layer is applied by vacuum evaporation on a substrate, which layer is solidified in such a manner as to obtain acceptor and donor sites on the surface of the semiconductor element.

Such a method is known from the French patent application No. 2.383.440. According to the known method, a mixture of semiconductor powders comprising metallophthalocyanine is prepared. Those powders are deposited onto an insulating substrate by vacuum evaporation in order to form a film of semiconductor elements. The substrate is also completed by adding the necessary electrical contacts. The elements can then be mounted in an electric circuit for fire detection.

With phthalocyanines it is well known that certain active sites are carriers of a slightly positive electric polarity. Those acceptor sites are situated near the center of the phthalocyanine molecules at the level of the metallic atom. On the other hand, other sites are situated near the periphery at the level of the nitrogen atoms and are carriers of a negative polarity.

When the phthalocyanine layer is applied by vacuum evaporation, a drawback of the known method is that the active surface of the film forming the semiconductor layer corresponds to its real geometry, which considerably reduces the number of active sites, preventing the gas from reaching one of the active sites of the phthalocyanine molecules and thus detecting a fire without flame.

The U.S. Pat. No. 4,381,440 describes also the application of phthalocyanine by painting a powder dispersed in a solvent. When the semiconductor elements are obtained in such a manner, the two types of active sites are accessible in such a manner that a fire with and without flames can be detected. Unfortunately the powders undergo a sintering in time, which progressively reduces the access to the different types of sites. The sensitivity constantly reduces by the ongoing sintering process and finally the sensors become completely insensitive.

The international application WO 95/05595 also describes a manufacturing method of such a semiconductor element. According to this method the sensitivity of the detector to the one or the other type of fire is obtained by the choice of the phthalocyanine applied on the substrate.

The object of the invention is to provide a method for manufacturing a semiconductor element enabling destabilization of the crystallization of the films obtained by vacuum evaporation in such a manner as to enable combustion gases to reach the active donor sites as well as the acceptor sites of the phthalocyanine molecules and to reduce the loss of sensitivity that the sensors undergo in time.

To this end, a method according to the invention of a semiconductor element is characterized in that, during the vacuum evaporation, the substrate is cooled to a temperature between −30° and 80° C., preferably −20° C. At this temperature, one obtains amorphous phthalocyanine layers which present an excellent sensitivity because, due to the low temperature, the molecules deposit in a random manner. The cooling of the substrate results in the fact that the kinetic energy of the phthalocyanine molecules, originating from the evaporation of the phthalocyanine, is practically immediately taken up when the molecules of the phthalocyanine enter into contact with the substrate. The molecules remain in this way blocked in their arrival position and do not reorient in a crystalline network. The semiconductor element thus manufactured presents donor and acceptor sites, which enable fire gases produced with or without flames to reach a site that is capable of detecting them.

A preferred embodiment of a method according to the invention is characterized in that the vacuum evaporation is realized by bringing the phthalocyanine source at a temperature of approximately 350° C. in a vacuum of approximately $10^{-4}$ during a period of time of approximately 10 minutes. The temperature essentially determines the speed at which the phthalocyanine will sublime and thus determine the deposition rate on the substrate. That speed also conditions the crystallization of the film. By adjusting the temperature, the crystallization speed is thus determined.

Another preferred embodiment of a method according to the invention is characterized in that the phthalocyanine layer is a mixture of different metallophthalocyanines. The small difference in form and dimension of the phthalocyanine molecules of, for example copper and cobalt, is sufficient to destablize the network and give rise to a polycrystalline growth.

Still another preferred embodiment of a method according to the invention is characterized in that for the substrate, an alumina substrate obtained by sintering alumina powders belonging to different granulometric classes is used. The use of powders belonging to different granulometric classes enables achievement a non planar surface of the substrate.

Yet another preferred embodiment of a method according to the invention is characterized in that the substrate used is a substrate based on sintered powders, which substrate is impregnated, before the application of the phthalocyanine, with a water-repellent substance that is capable of polymerizing in the residual pores that are present after sintering. The use of substrates based on sintered powders such as alumina, presents the drawback of having several pores and interstices between the alumina grains. When the humidity of the ambient atmosphere increases up to 70% of relative humidity, those pores can be the seat of capillary condensation. Under these circumstances, the electrical resistance of the alumina substrate diminishes considerably so as to become lower than the one of the sensitive layer. Those two resistances being connected in parallel, it will be the weakest, in this case the one of the substrate, which will become determinant. In order to avoid this effect, the substrate is first impregnated with a water-repellent substance capable of polymerizing in the pores of the sintered alumina. A later capillary condensation will be thus avoided.

Yet another preferred embodiment of a method according to the invention is characterized in that the substrate is a silicon substrate covered by an insulating layer of which the surface has been rendered porous and rough. The intrinsic resistive value of the layers with which the silicon can be covered makes that substrate particularly suitable.

The invention will now be described in more detail by means of the description given hereunder. This description refers to drawings wherein:

FIG. 1a) and 1b) illustrate the organization of the film on a smooth substrate;

FIG. 1c) and 1d) illustrate the crystallographic structures of the copper phthalocyanine;

In the drawings, the same reference number has been assigned to the same or an analogous element.

The sensors pursuant to this invention, such as for example fire detection sensors, generally comprise a semiconductor element. This element is formed by an insulating substrate having a specific resistive value of at least $10^{12}$W cm. On this substrate a phthalocyanine layer is applied.

The phthalocyanine has the following properties: in perfect vacuum, it behaves like an insulator, and thus its conductivity is almost zero. If it is put into contact with a gaseous agent, a possible adsorption of the gas at the surface is possible, which influences on its conductivity and thus its resistance.

Thus, when the adsorbed gas is an electron acceptor such as $O_2O_3$, $SO_2$, $NO_x$. . . , there is an electron transfer from the film to the adsorbed molecules, the number of positive charges in the layer increases and facilitates the electron transfer from one molecule to another, which increases the conductivity or reduces the resistance. That is what is observed when a phthalocyanine copper layer is placed in the atmosphere:the elements with an acceptor character, present in the ambient air, are absorbed on the film surface and give an extrinsic p-type semiconductor character to the phthalocyanine.

Contrarily, when the phthalocyanine layer is in the air and then later contacts a donor gas, such as $NH_3$, under normal conditions, a reduction of the conductivity is observed due to annulment of the acceptor gas effects.

This resistance variation of the phthalocyanine in the function of the present gas can be used for several household applications such as fire detection.

Thus, the copper phthalocyanine (CuPc) enables one to distinguish a fire with flame from one without flame: indeed, during a fire without flame, the combustion is incomplete and the produced gases are essentially donor gases. By adsorbing on the film, the latter gives electrons away and reduces the extrinsic p-type semiconductor character that the phthalocyanine has in contact with the atmosphere. The conductivity of the phthalocyanine thus substantially decreases.

In case of a fire with flames, on the contrary, essentially highly oxidized gases are created, thus acceptor gases which increase the number of p-type carriers of phthalocyanine, and absorb thereon:the conductivity of the layer thus increases.

Figure 9:
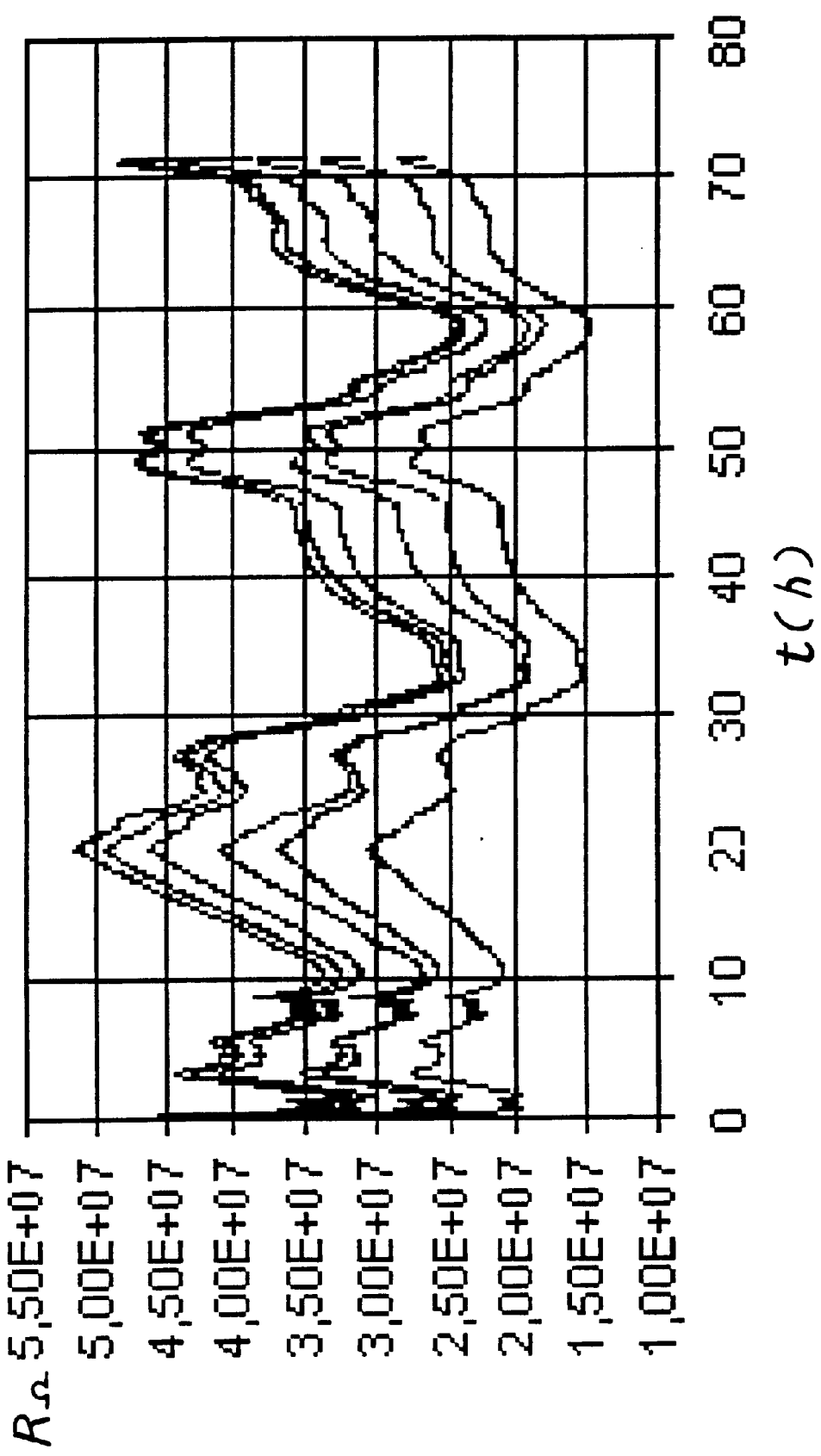
FIGS. 9 illustrates a change in resistance of six sensors submitted to the ambient in function of time.

A fire sensor based on CuPc placed in a normal atmosphere, i.e. without any fire, will also undergo resistance fluctuations. Indeed, during the day, the atmosphere composition can substantially change. Moreover, according to the seasons or the locations, the atmospheric conditions can greatly change. The composition of the atmosphere is thus not a constant parameter, which will thus induce variations in the resistance of the sensor. A variation example, in function of time, of the resistance of six sensors placed in the ambient, is illustrated in FIG. 9.

These important amplitude fluctuations render the use of resistance thresholds for starting a fire detection alarm impossible. Such thresholds can, however, be used for household applications and, for instance, for starting a ventilation device, an air-conditioning apparatus, or an air-cleaning device, or can also be used for detecting the presence of a major polluter. Natural variations can, however, partially be eliminated by the interposition of specific filters. Thus, for example, one can use as a filter for eliminating ozone a grid impregnated with indigo. In the case of fire detection, a processing of the signal based on the dynamics of these detected phenomena is required.

For this purpose, the "ratio" r has been defined which characterizes the dynamic evolution of the sensor:

$$r = \frac{R(t)}{R(t-15)}$$

where

R(t) represents the resistance of the sensor at the time t, and

R(t-15) represents the resistance of the sensor at the time t-15 sec.

It is the ratio r which enables one to determine the sensitivity of the layer. The behavior of its value in time enables one to characterize the stability notion.

Thus defined, the ratio r given per sensor of fire With flame will be lower or equal to 0.85, and for a fire without flame higher or equal to 1.25. These values can ever be obtained as a result of ambient air fluctuations (0.97<r <1.06).

The known technology uses phthalocyanine powders, which give good results, but the evolution in time cannot be controlled. Thus, as time passes, the powders have a tendency to undergo a progressive sintering, which reduces the specific surface and thus the active reaction surface. The sintering thus induces a progressive sensitivity reduction which cannot be recuperated by electronic control signals. The ratios r become close to 1 as time passes.

At long term, this sensor type becomes useless and can no longer be used for highly sensitive purposes which relate to the security of goods and persons such as fire detection.

The use of phthalocyanine in the form of "powders" enjoys a considerable advantage, because the specific surface is in the beginning very important as is its sensitivity. Moreover, each grain constituted of set up phthalocyanine molecules, is accessible to the gas at all its faces. Consequently, all active sites, donors and acceptors, central and peripheral of the molecules are accessible.

This accessibility to all reaction sites of the molecules is extremely important, because it enables the detection of all kind of fires with or without flame. Unfortunately, in the "powders" configuration, the evolution in time is such that the sensitivity rapidly decreases.

On the other hand, with the well known detectors situated on a smooth substrate, the active film surface corresponds to the geometrical real surface, which substantially reduces its reactivity and thus its sensitivity. On classical and smooth silicon, covered by an insulating oxide layer and other insulators, such as silicon nitride, the results are, such as in the two preceding cases, very random and not all fire types can be detected. Thus, for example, the ratio r is excellent in the case of a fire with flames (r<0.6). On the other hand, for a smoldering fire without flame, the ratio (r@1.1) is less good, and consequently the fire will be difficult to detect because the ratio is close to that of the ambient fluctuations.

It is also well known that the nature of the substrate employed and its manufacturing conditions have a large influence on the crystallization of the film and thus on the reactivity of the sensitive layers. Thus, John D. Wright in his book "Progress in surface science" published at Maxwell Pergamon Macmillan, describes in the article (Vol. 31 pp. 1 to 60) "Gas adsorption and Conductivity of Phthalocyanines" the influence of these operating conditions on the nature and the morphology of the obtained films. This study has been realized on totally different substrates because it relates to muscovite or alkaline salts. The growth principles of the layer are nevertheless apparent and demonstrate the importance of the nature of the substrate surface and the operation conditions.

Figure 1A:
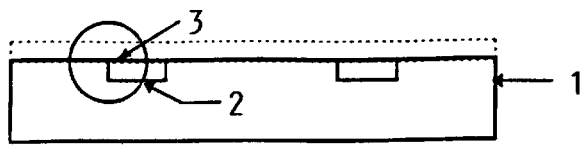

Usually, all the gas sensors, the sensitive layers of which are deposited by evaporation under vacuum, such as metallic oxide semiconductor or organic semiconductor (phthalocyanine), are deposited on substrates which have as smooth a surface as possible . These surfaces are thus perfectly smooth, clear from all uncleanliness and, in some cases, the electrodes (2) are even embedded in the substrate (1), so as to obtain a film (3) which is perfect on the whole surface, such as illustrated in FIG. 1a.

Figure 1B:
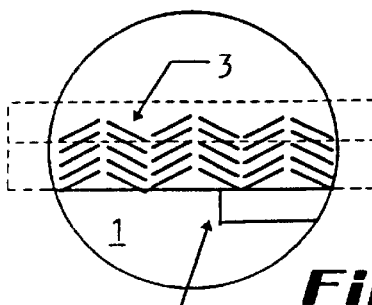

The thus obtained films provided by vacuum evaporation on such substrates have an ordered structure, the active surface of which is limited to the real geometric surface, as illustrated in FIG. 1b. This prevents access of the gases right from the beginning to all types of reaction sites of the phthalocyanine molecules. Indeed, the phthalocyanine molecules assume a chevron (3) structure having an upper layer which blocks the access of gas to the lower layers and thus to the active peripheral sites' of the molecules. Indeed, during primary adsorption the peripheral sites lower layers do not contribute, or contribute little, to the change of the resistance or the conductivity of semiconductor.

Figure 1C:
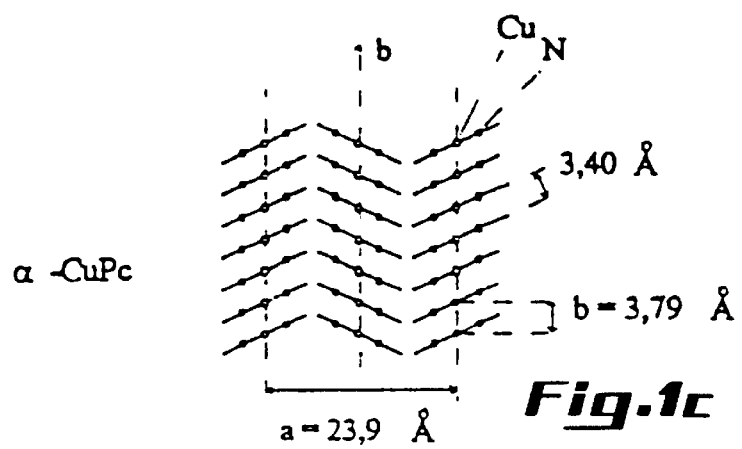
Figure 1D:
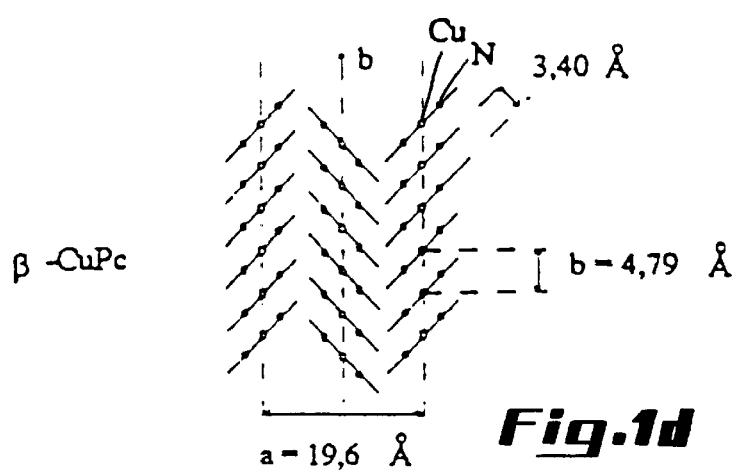

FIGS. 1c) and 1d) illustrate the crystallographic structure of the copper phthalocyanine type a. As can be learned from FIG. 1c, the copper atom Cu is situated in the center and the four nitrogen atoms at the periphery of the molecule. The distance between two superposed copper atoms is 3.79 Å and the distance between two superposed nitrogen atoms is 3.40 Å. Because the metal atom, namely the copper, is in the middle, the acceptor site is in the middle, whereas the donor sites, formed by the nitrogen atoms, are situated at the periphery. The different layers forming the phthalocyanine copper molecule are well ordered, and the same disposition of atoms is found in each layer. Even crystallographic modifications leading to other layer structures, as for example the one of the copper type b phthalocyanine, illustrated in FIG. 1d), do not modify the accessibility to the donor and acceptor sites.

The invention consists in using means enabling the destabilization of the crystallization of the layers in such a manner as to enable gases to reach both the acceptor sites and the donors sites of the molecule. Thus, the central sites at the level of the metallic atom and the peripheral sites at the level of nitrogen atoms should be accessible. Moreover, an additional purpose of the invention is to reduce the sensitivity loss over time that the semiconductor elements undergo.

In order to reach this object, the invention goes in the opposite direction from the accepted principles.

The invention consists notably in destabilizing considerably the crystallization of the phthalocyanine film, when the latter is solidified on the substrate. One way to destabilize the crystallization of the phthalocyanine film is to use substrates on which voluntarily a certain number of faults has been created in such a manner as to obtain on these substrates a sensitive layer of which the random crystallization is not continuous and not uniform. The random character of the crystallization is defined by the nature, the roughness and the superficial pretreatment of the substrate. The orientation texture of the crystals of the layer, applied on a rough substrate, will no longer lead to an orderly orientation otherwise obtained on such a smooth substrate, but it will be constituted of polycrystalline aggregates presenting random crystallizations.

A non-uniform substrate surface is, for example, obtained by sintering alumina powders ($Al_2O_3$) with different granulometric powder classes. The alumina substrate is, for example, obtained by sintering powders, having a granulometry situated in a range between 1 and 3 $\mu$m. Powders having a granulometric class of 1 to 8 $\mu$m can also be used.

Thus, sensitive phthalocyanine layers can be applied on alumina substrates provided with silk-screened golden electrodes, starting from pastes composed of gold strips, the cohesion of which is insured by an organic binder. These pastes are annealed at high temperature (T>800° C.). Also the electrodes present a roughness which gives to the thus realized set a considerable roughness which can be measured and visualized by an electronic microscope.

Thus, for example, the average roughness measured on the two different types of alumina substrate, is comprised between 0.4 and 0.7 $\mu$m for the alumina and in the order of 0.2 $\mu$m for the electrodes.

Figure 2:
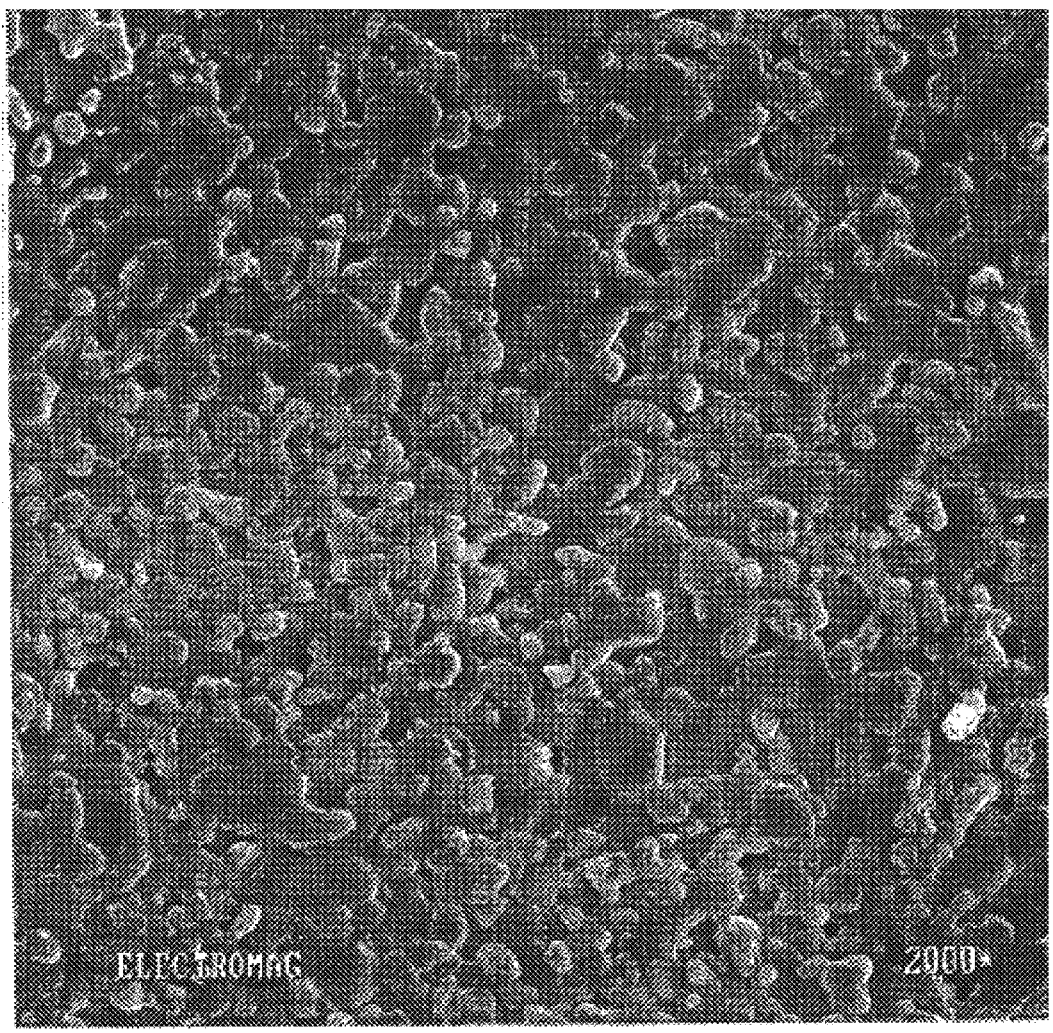
FIGS. 2 and 3 illustrate, at a larger scale, the rough surface and the grain profile of the used substrate in the application of the method according to the invention.
Figure 3:
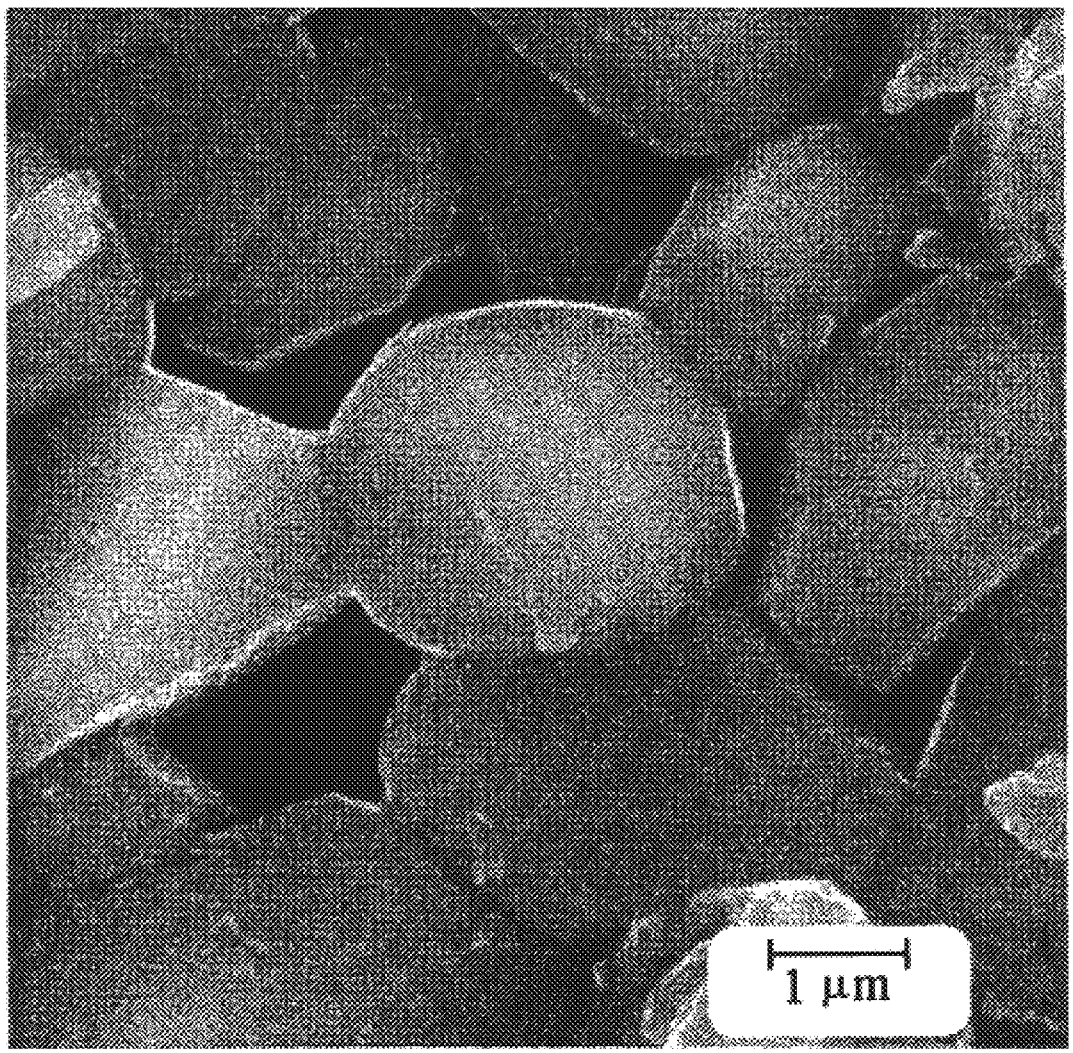

FIGS. 2 and 3 illustrate the rough surface and the grain profile which are preserved after the substrate sintering. These figures have been obtained by electronic scanning microscopy. FIG. 3 represents a detail of FIG. 2 five times enlarged. As can be seen from these figures, the substrate surface thus prepared is completely disturbed and presents no flatness.

On those such prepared substrates, thin layers of phthalocyanine are applied (which are of a few hundred to a few thousand angstroms) in order to form a completely disorganized layer having a large sensitivity and presenting acceptor and donor sites on their surface. Indeed, if the thickness of the layer becomes too large, it will organize itself, which leads to a loss of the advantage of the rough surface and reduces its sensitivity, thus causing situation similar to the one with a smooth substrate.

Figure 4A:
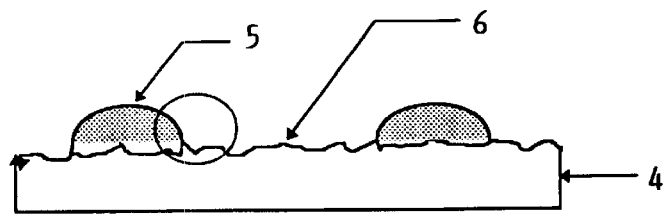
FIGS. 4a and 4b show a detail of the phthalocyanine film organization on a rough substrate.
Figure 4B:
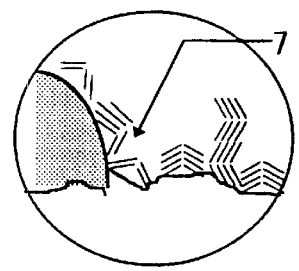

FIG. 4 shows an example of a semiconductor element obtained by application of a method according to the invention. The substrate 4 comprises a rough surface 6, on which electrodes 5 as well as the phthalocyanine layer 7, which no longer has a uniform character, have been applied. The thin layer thus obtained on the rough substrate is totally disorganized and forms a "polycrystalline aggregate" on the substrate.

Figure 5:
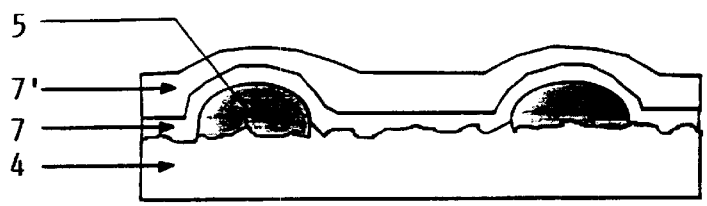
FIGS. 5 illustrates a substrate on which a too thick layer has been applied.

FIG. 5 shows an example where a disorganized phthalocyanine layer 7 is too thick and is thus covered by an organized layer 7' destroying the effect of the rough character of substrate 4.

Before being applied on the substrate, the phthalocyanine must be carefully purified in order to remove impurities which could lead to sublimation during the vacuum evaporation. This aspect is very important for the reproduction of the realized sensors.

Figure 11:
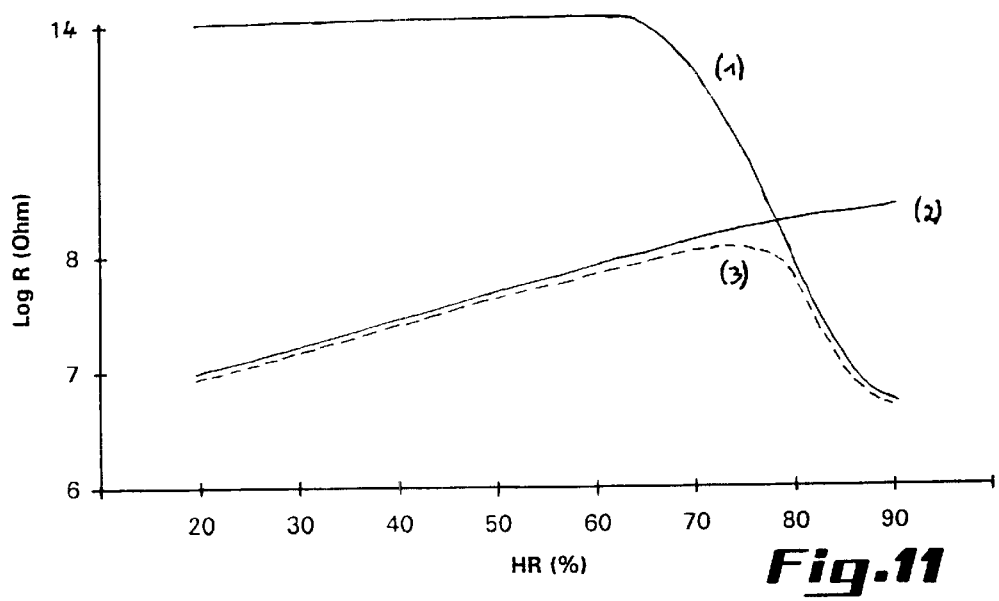
FIG. 11 illustrates the evolution of the electrical resistance of different components of the semiconductor element in function of the relative humidity.

The use of substrates on the base of sintering powders such as alumina has the drawback of presenting several pores and interstices between the alumina grains. When the humidity of the ambient atmosphere increases up to 70% relative humidity, these pores can be the seat of capillary condensation. Under these circumstances, the electrical resistance of the alumina substrate substantially decreases and becomes lower than the one of the sensitive layer such as illustrated in FIG. 11, which shows the evolution of the electrical resistance (Log R) of the different components as a function of the relative humidity. Curve (1) illustrates the decrease of the substrate resistance, curve (2) shows the phthalocyanine layer resistance, and curve (3) the resistance of the substrate with the phthalocyanine layer as a whole. Because the resistance of the substrate and the resistance of the phthalocyanine layer are applied in parallel, it will be in this case the weakest, i.e. the resistance of the substrate, which becomes determinant, as illustrated by the curve (3).

This influence of atmospheric humidity can be avoided by impregnating, before the phthalocyanine layer application, the alumina substrate with waterproof substances suitable to polymerize in the residual pores, which are present on the sintered alumina. Capillary condensation can thus be substantially reduced. The waterproof substance used to block the substrate pores, is for example constituted of polysiloxane.

Figure 12:
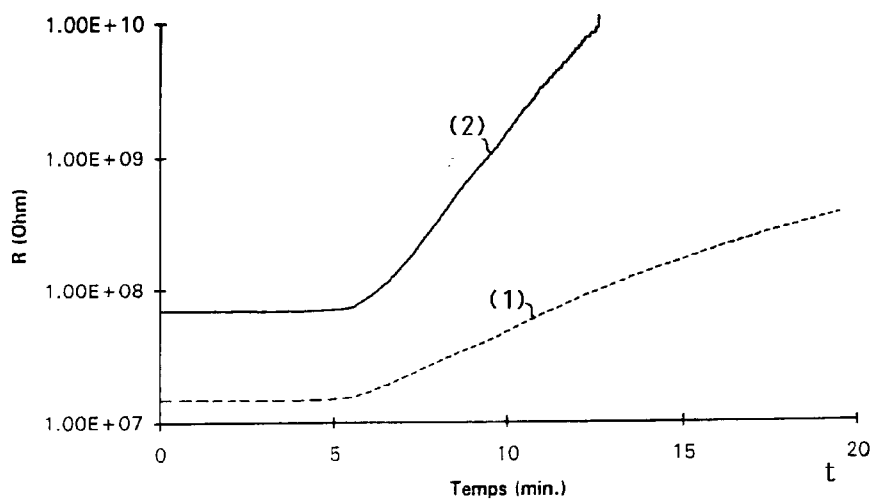
FIGS. 12 and 13 illustrate the evolution of the electrical resistance of the different components of the semiconductor element in time when a fire without flame is declared.

A surprising effect of this impregnation resides in the fact that the semiconductor layers applied on the processed substrates present a much more important sensitivity to fire without flames. This effect can be explained by the fact that the polysiloxanes cover totally the alumina grains present on the surface. This modification of the surface favors a particular crystallization of the phthalocyanine, which leads to a larger number of reaction sites sensitive to the action of gas emitted by fires without flame. This effect is illustrated in FIG. 12 where the curves (1) and (2) illustrate the resistance evolution as a function of the time (t) in the presence of fire without flame for a detector on a non-impregnated substrate (1) on an impregnated substrate (2).

According to an alternative embodiment, the method according to the invention also allows use of a smooth substrate, the surface of which is subjected to attack by acid baths, as for example by hydrofluoric acid (HF) when it concerns a substrate of glass or of silicon. One can also apply to the latter, for example by means of laser, grooves in order to render the surface rough.

Figure 6:
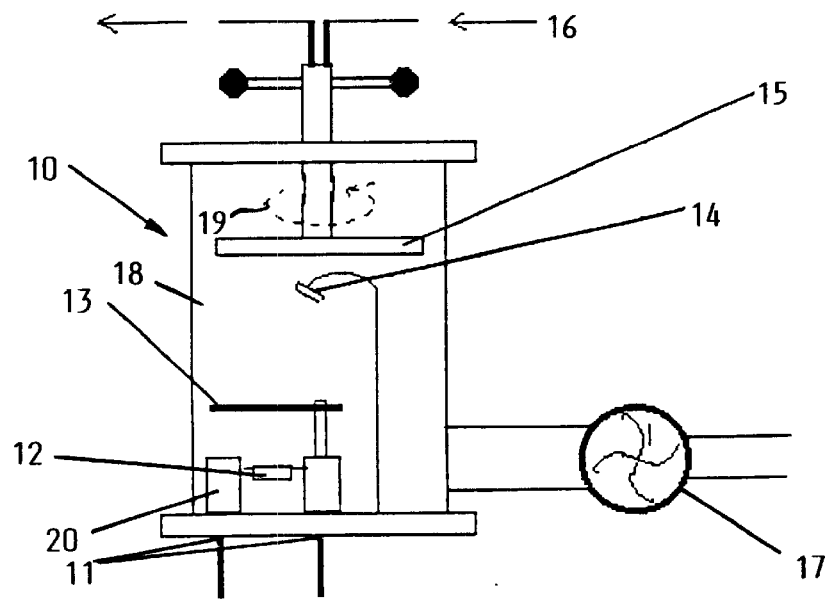
FIGS. 6 illustrates an example of a device enabling the application of the method according to the invention.

FIG. 6 illustrates an example of a device enabling the application of the process according to the invention. The device 10 comprises an input 11 for applying thereon an electric current. The device is provided for enabling a vacuum evaporation and comprises therefore a cap 18 under which several components are placed. A pump 17 enables the pumping of air under the cap in order to create a vacuum preferably of $10^{-4}$ Pa.

A carrier 20 supporting the source 12 of the phthalocyanine is disposed under the cap 18. The carrier comprises heating means, for example formed by an electrical resistance connected to the input 11. On top of the source 12 there is a shutter 13 for reducing the supply of evaporated phthalocyanine supplied by source 12. A quartz oscillator 14 also placed under the cap enables measurement of the quantity of applied phthalocyanine during evaporation. Indeed, the oscillator frequency changes as a function of the thickness of the applied layer.

The substrates 15 are fixed on a substrate carrier 19, also applied under the cap 18. In order to maintain the substrate carrier at a predetermined temperature, a heat fluid carrier duct 16 is provided, which is connected to the substrate carrier. In this case, the substrate carrier 19 is driven into rotation by means of a motor (not illustrated). This enables equal distribution of the phthalocyanine on the whole of the substrate.

Before being covered with the phthalocyanine layer, the substrate is cleaned in order to remove all uncleanness which could interfere with the phthalocyanine layer. This cleaning is for example realized by means of ultrasonic waves, which enable detachment of the uncleanness which sticks on the substrate.

The cleaning can also be realized by means of a solvent such as for example trichloroethylene, acetone or acid.

Figure 10:
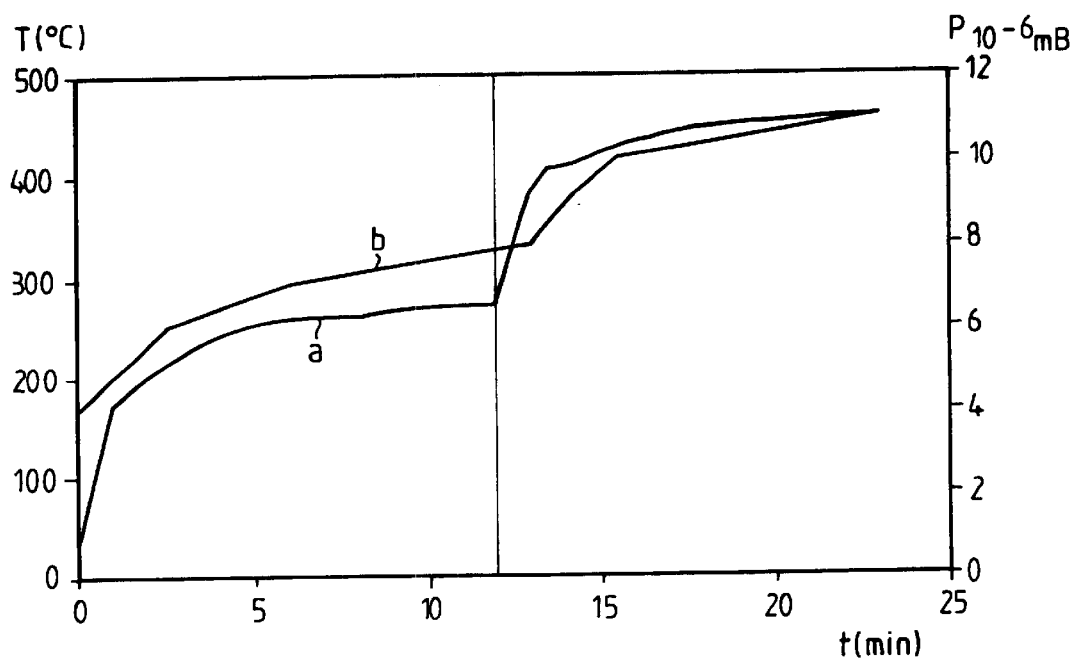
FIGS. 10 illustrates the evolution of the partial pressure of the phthalocyanine during evaporation in function of the nacelle.

The vacuum evaporation is realized by bringing a nacelle, constituting the source 12, to a temperature of approximately 350° C. by a Joule effect under a vacuum in the order of $10^{-4}$ Pa. By controlling the temperature of the nacelle, it is possible to regulate the evaporation speed. FIG. 10 illustrates the evolution of the partial pressure $P(_b)$ in the time (min) of the phthalocyanine layer as a function of the nacelle temperature $T(_a)$, It can thus be established that at a temperature between 290° and 400° C., evaporation takes place. Indeed, the higher the temperature of the source, the greater the evaporation of the material. The speed thus equally conditions crystallization of the phthalocyanine film applied on the substrate. The best results are obtained at reduced speed. Thus, for example, a film having a thickness of 500 Å is obtained with an evaporation time of 10 minutes with a temperature of 350° C. and a pressure of $10^{-4}$ Pa. This corresponds to an application speed going from a few molecules to ten per minute, depending on their orientation in the crystalline network. The time during which the application takes place is controlled by the opening time of the shutter 13.

Vacuum evaporation enables evaporation of the substance by sublimation at gaseous state and acquisition of the desired random character of the application.

The applied phthalocyanine quantity and thus, in a certain manner, the thickness of the applied layer, will determine the sensitivity of the sensor using the element formed by semiconductors. Indeed, an equivalent layer with a thickness of 100 Å will enable the detection of smoke of one single cigarette, whereas a thickness of 250 Å will be less sensitive to ambient fluctuations. The quantity of material applied per $cm^2$ on the substrate is 1.4 µg and 35 µg for a layer of 100 Å by 2500 Å. The thicker the layer, the weaker the sensor sensitivity.

The temperature of the substrate carrier (15) presents also a considerable importance for the crystallization of the layers. This temperature can fall between −30 and +80° C. depending on the type of used substrate. For example, with a temperature of substrate at −20° C., amorphous layers are obtained, which present an excellent sensitivity, because the molecules are applied in a completely random way. They also present different orientations to the action of gas, orientations which are absolutely suitable to obtain a phthalocyanine layer having acceptor sites and donor sites.

Indeed, when the substrate is cooled to a temperature lower than 0° C., the kinetic energy of phthalocyanine molecules coming from the evaporation of source 12, is practically immediately taken up when the molecules enter into contact with the substrate. This causes the molecules to remain fixed in their arrival position without reorienting themselves in a crystalline network. An amorphous layer is thus obtained instead of an ordered crystal. In this amorphous layer all orientations and thus all different site types will be present.

Figure 13:
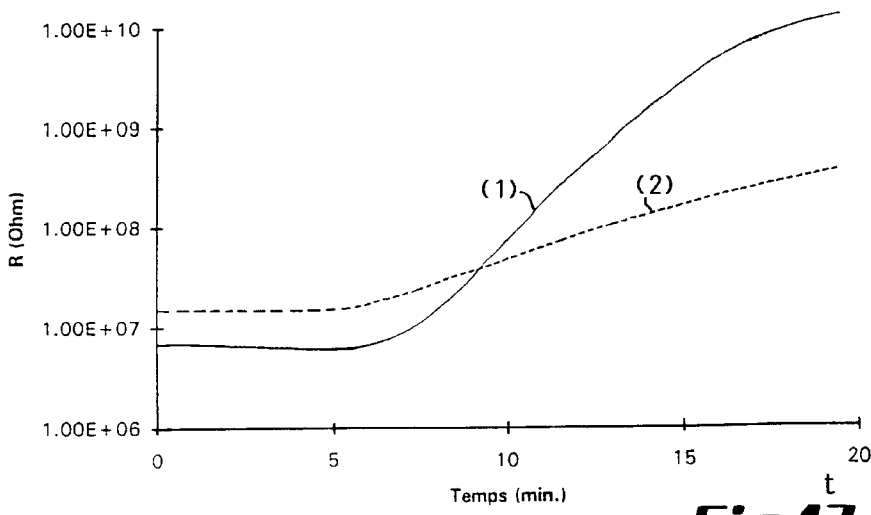

FIG. 13 illustrates the difference in sensitivity obtained by a sensor realized by cooling the substrate during the application of the sensitivity layer. The resistive value R of the sensor (curve (1)) realized by cooling the substrate increases more rapidly in time t in presence of a fire without flame than the resistive value R of a sensor (curve (2)) obtained at the ambient temperature.

Figure 7:
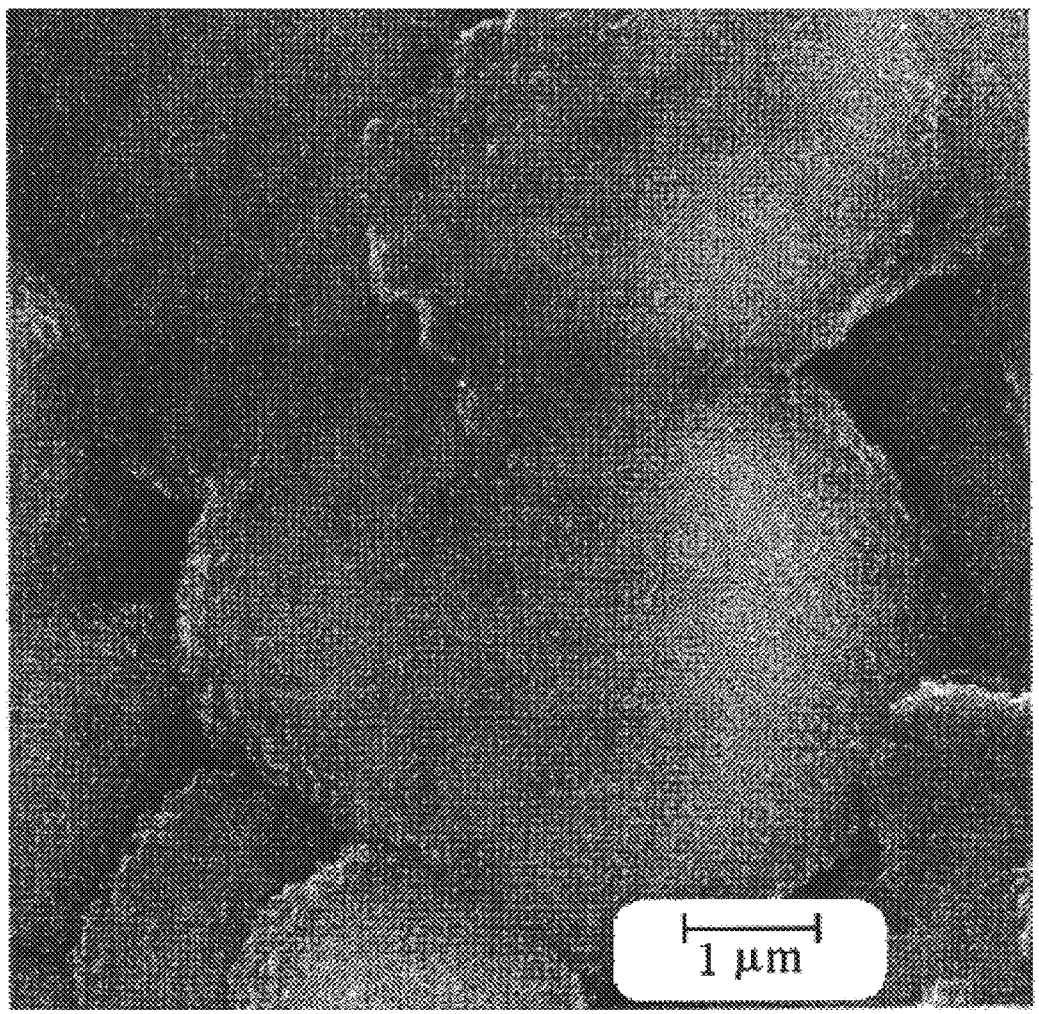
FIGS. 7 and 8 illustrate, at a larger scale, a semiconductor element obtained by application of the method according to the invention.

FIG. 7 illustrates the result obtained by application of the method according to the invention and illustrates at the same time the difference from the known technique. As shown in the figure, each alumina grain is covered by micropolycrystalline aggregates separated from one another, which are present in the form of a flocculent foam, very open-pored, porous and having a large specific surface particularly favorable to the behavior of the sensor. This large specific surface enables a favorable exchange with ambient gas and also increases the sensor sensitivity.

At this stage, a sensitive layer formed of polycrystalline aggregates is obtained, of which the characteristics after manufacturing are as follows

| r ambient: | $0.97 < r < 1.06$ |
|---|---|
| r fire with flame (rFAF): | $0.60 < r < 0.75$ |
| r fire without flame (rFSF): | $1.50 < r < 3$ |

However, these sensors, notwithstanding their very good sensitivity (r FAF<<<r ambi <<<rFSF), can present a stability deterioration in time: thus, after 6 months, the obtained ratios are as follows:

| r ambient: | $0.97 < r < 1.06$ |
|---|---|
| r fire with flame (rFAF): | $0.75 < r < 0.85$ |
| r fire without flame (rFSF): | $1.20 < r < 1.40$ |

It has to be noted that as time passes, the fire ratios become progressively close to 1, which means that a small loss of sensitivity to fire is observed. This ratio evolution is accompanied by an increase in resistance of the sensors, which becomes inconvenient for use with classical electronics.

Figure 8:
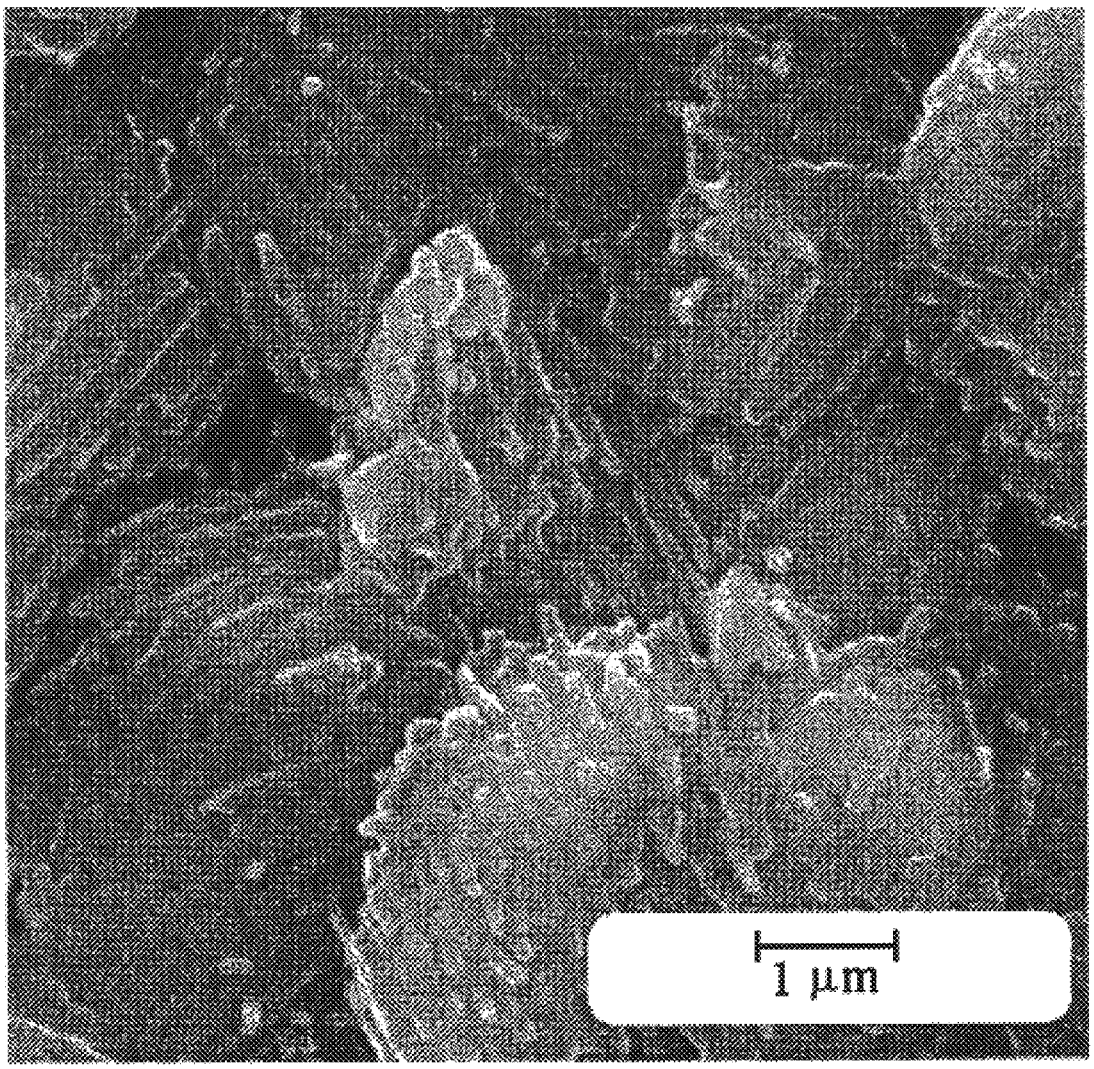

For this reason, during the manufacturing and/or after this manufacturing, the sensors undergo several processings in order to stabilize them over long periods of time. Among those processings, one comprises a post-manufacturing thermal processing. In this processing, the phthalocyanine layers applied under vacuum on these substrates are then submitted to a thermal treatment (for example 8 hours at 150° C.) so as to stabilize the structure. Indeed, it can be observed that this thermal processing reduces somewhat the sensitivity of the formed films but allows them to be maintained longer over time by blocking the crystallization. The obtained crystallization under these conditions is reproduced in FIG. 8 where a more pronounced, and in all directions oriented, crystallization can clearly be observed.

The use of sensors in which the substrate has been cooled during manufacturing presents the following characteristics

| r ambient: | $0.97 < r < 1.06$ |
|---|---|
| r fire with flame (rFAF) | $0.70 < r < 0.85$ |
| r fire without flame (rFSF) | $1.30 < r < 1.50$ |

No further considerable evolution of the sensitivity of the fire sensitive layer can be observed.

The aforementioned results have been obtained on alumina substrates. Similar results can be obtained on other substrates, such as, for example, substrates of glass or silica, of which the surface has been rendered porous. This operation can, for example, easily be realized by electrochemical anodizing of silicon wafers in hydrofluoric acid solutions (HF). These wafers are submitted to oxidation processing, in such a manner, as to form an oxide layer ($SiO_2$), or are submitted to another application of an insulating material such as silicon nitride ($Si_2N_4$) or $Al_2O_3$. The application of an oxide layer or an insulator is necessary due to the semiconductor properties of silicon. It is therefore necessary to insulate the silicon substrate from the applied phthalocyanine layer. The thus realized substrates can then receive the phthalocyanine layer which, due to the roughness of the realized surface, also presents polycrystalline aggregates.

An alternative to increasing sensitivity of the film by processing of the substrate is deforming the film crystalline network by simultaneously evaporating a mixture of different phthalocyanines. Thus, one can introduce within the heated nacelle, which constitutes the material source in the vacuum evaporator, a mixture of phthalocyanines that are preferably pure, for example 95% by weight of copper and 5% by weight of cobalt. During such an application, the sensitive film will form itself gradually by applying phthalocyanine cobalt molecules in between the network of the copper phthalocyanine. The low difference in shape and dimension of these molecules with respect to the copper phthalocyanine is sufficient for destabilizing the network, thus giving rise to a polycrystalline growth. The sensitivity of the thus obtained films is largely increased.

| r ambient: | $0.97 < r < 1.06$ |
|---|---|
| r fire with flame (rFAF) | $0.50 < r < 0.75$ |
| r fire without flame (rFSF) | $1.60 < r < 3$ |

Such mixtures can be realized starting from hydrogenated or metallic phthalocyanines and as for example nickel, iron, zinc, lead; etc. The more different the co-evaporated molecule, the more important is the destabilization. Each mixture, however, imposes in each case a precise study of the proportion and the evaporation speed.

Besides phthalocyanine mixtures, it is also possible to use phthalocyanines of different metals, as for example phthalocyanine of iron, lead, nickel or cobalt.

The comparison of the obtained results under such conditions (rough substrates, co-deposition, thermal processing) shows that formed aggregates are completely different.

This crystallization is however determined by the substrate of which the surfaces of the microscopic scale present different angles to each other and probably induce an epitaxic growth phenomenon according to the crystal orientations of the substrate.

This type of result can also be obtained with substrates other than alumina. They should however fulfill a certain number of conditions. The electrical resistance of the substrate should be substantially higher than the resistance of the sensitive layers (at least a factor 100).

The sensors based on phthalocyanine realized by the application of the method according to the invention can also be used for household purposes. One can then work by thresholds instead of by ratios. The sensors for household purposes serve for example for air conditioning of the ambient air. Above or beneath the predetermined resistance threshold, the sensor becomes active and will start a signal for turning on, for example, a ventilation or purification system or switch on an alarm signal. As illustrated in FIG. 9, the ambient evolutions of the sensors are situated in a normal ambient atmosphere in a range between $1.10^7$ and $8.10^7$ W. Therefore each deviation higher or lower than these values will cause the generation of a signal. Thus, for example, the smoke of a cigarette will let the resistance increase to a value above $8.10^7$W and a polluter such as chlorine or a Nox will reduce the resistance to less than $10^7$W.

I claim:

1. A method for manufacturing a semiconductor element for detection of a fire with or without flame, comprising applying a phthalocyanine layer under vacuum evaporation on a substrate that has an irregular surface, solidifying said layer without annealing to obtain on said surface irregular acceptor sites and donor sites, and maintaining said substrate during vacuum evaporation at a temperature between about −30° C. and about 80° C.

2. A method for manufacturing a semiconductor element for detection of a fire with or without a flame, comprising applying a phthalocyanine layer under vacuum evaporation on a substrate that has an irregular surface, solidifying said layer without annealing to obtain on said surface acceptor sites and donor sites, and maintaining said substrate during vacuum evaporation at a temperature between about −30° C. and about 80° C., wherein said vacuum evaporation is realized by bringing a phthalocyanine source at a temperate of substantially 350° C. under vacuum of substantially $10^{-4}$ Pa during a time period of approximately 10 minutes.

3. A method for manufacturing a semiconductor element as claimed in claim 2, wherein after applying said layer under vacuum evaporation, said substrate and said layer are subjected to a thermal processing for their stabilization.

4. A method for manufacturing a semiconductor element as claimed in claim 1, wherein said layer comprises a phthalocyanine mixture of different metals.

5. A method for manufacturing a semiconductor element as claimed in claim 1, wherein the quantity of phthalocyanine applied on said substrate is between 1.4 $\mu$g/cm$^2$ and 35 $\mu$g/cm$^2$.

6. A method for manufacturing a semiconductor element as claimed in claim 1, wherein said substrate is alumina obtained by sintering of alumina powders belonging to powders of different granulometric classes.

7. A method for manufacturing a semiconductor element as claimed in claim 1, wherein said substrate is a substrate based on sintered powders, which substrate is impregnated, before said application of the phthalocyanine, with a water-repellent substance suitable to polymerize within the residual pores, present between grains of the powders after sintering of the powders.

8. A method for manufacturing a semiconductor element as claimed in claim 7, wherein said water-repellent substance comprises polysiloxane.

9. A method for manufacturing a semiconductor element as claimed in claim 1, wherein said substrate is a silicon substrate covered by an insulating layer, and having a rough surface.

10. A method for manufacturing a semiconductor element as claimed in claim 7, wherein said surface of said silicon substrate is made rough by electrochemical anodizing of a silicon plate in a hydrofluoric acid solution, followed by oxidation.

11. A method for manufacturing a semiconductor element as claimed in claim 1, wherein said substrate is maintained at a temperature of about −20° C.

12. A fire detector comprising a semiconductor element produced by the method as claimed in claim 1, wherein said phthalocyanine layer has a sensitivity r lower or equal to 0.85 for a detection of a fire with a flame and higher or equal to 1.2 for a detection of a fire without flames, wherein r is a quotient between a detector resistance R(t) at a time t and divided by a detector resistance R(t-15) at t-15 seconds.

* * * * *